(12) United States Patent
Mandecki et al.

(10) Patent No.: US 8,353,917 B2
(45) Date of Patent: Jan. 15, 2013

(54) APPARATUS AND METHOD TO DELIVER A MICROCHIP

(75) Inventors: Wlodek Mandecki, Princeton, NJ (US);
Hanan Davidowitz, Princeton, NJ (US);
Maryann Gruda, Yardley, PA (US);
Edward Kuspiel, Princeton, NJ (US);
Joseph Nolfo, Princeton, NJ (US); Ziye (Jay) Qian, Monroe Township, NJ (US);
Gary H. Reitnauer, Quakertown, PA (US)

(73) Assignee: PharmaSeq, Inc., Monmouth Junction, NJ (US)

( * ) Notice: Subject to any disclaimer, the term of this patent is extended or adjusted under 35 U.S.C. 154(b) by 40 days.

(21) Appl. No.: 12/889,007

(22) Filed: Sep. 23, 2010

(65) Prior Publication Data

US 2011/0077659 A1    Mar. 31, 2011

Related U.S. Application Data

(60) Provisional application No. 61/245,953, filed on Sep. 25, 2009.

(51) Int. Cl.
*A61B 17/00* (2006.01)
(52) U.S. Cl. ..................................................... 606/117
(58) Field of Classification Search .............. 606/117, 606/181, 182, 183; 604/57, 59, 60, 61, 891.1
See application file for complete search history.

(56) References Cited

U.S. PATENT DOCUMENTS

| | | | | |
|---|---|---|---|---|
| 5,484,403 A | * | 1/1996 | Yoakum et al. | 604/59 |
| 5,772,671 A | * | 6/1998 | Harmon | 606/117 |
| 6,270,472 B1 | * | 8/2001 | Antaki et al. | 604/61 |
| 6,273,712 B1 | | 8/2001 | Rach et al. | |
| 7,098,394 B2 | | 8/2006 | Armer et al. | |
| 2002/0049411 A1 | * | 4/2002 | Lamoureux et al. | 604/164.01 |
| 2003/0062988 A1 | | 4/2003 | Mandecki et al. | |
| 2003/0063551 A1 | | 4/2003 | Takeuchi | |
| 2006/0004370 A1 | | 1/2006 | Bagby | |
| 2008/0254400 A1 | | 10/2008 | Scherl et al. | |
| 2009/0112179 A1 | | 4/2009 | Zoltan et al. | |

OTHER PUBLICATIONS

International Search Report and Written Opinion mailed Jun. 15, 2011 for Application PCT/US2010/049942.

* cited by examiner

*Primary Examiner* — Ryan Severson
*Assistant Examiner* — Jonathan W Miles
(74) *Attorney, Agent, or Firm* — Moser Taboada (57) ABSTRACT

Provided are methods and apparatus including an injector system adapted for injecting a microchip comprising: an inserter comprising a rod or tube having a proximal and distal end and having a point at the distal end that defines a skin-piercing side of the inserter; a means for engaging the microchip near the distal end of the inserter, but removed in the proximal direction from the distal tip of the inserter, which means prevents rotation of an engaged microchip in two or three axes of rotation; and means for releasing the microchip from the inserter once the inserter has been inserted into a perforatable substrate.

19 Claims, 6 Drawing Sheets

APPARATUS AND METHOD TO DELIVER A MICROCHIP

CROSS-REFERENCE TO RELATED APPLICATIONS

This application claims priority to U.S. Provisional Patent Application Ser. No. 61/245,953, filed Sep. 25, 2009, which is incorporated by reference herein in its entirety.

Embodiments of the present invention generally relates to methods for subcutaneously delivering a sided, planar microchip and devices for causing such delivery.

As described in U.S. Pat. No. 7,098,394, very small, light-triggered transponders are available to provide identifiers, for example as identifiers used in conjunction in nucleic acid assays. These have proven to be stable under physiological conditions. Hence, they can be used as implanted tagging devices for animals.

Radio frequency identification devices have been in use for some time, including for animal tagging. Systems are available for example from Avid Technology, Inc. (Tewksbury, Mass.), Lutronic International (Rodange, Luxenbourg) and Bio Medic Data Systems, Inc. (Seaford, Del.). In animal use, these systems are encapsulated, such as in biocompatible glass. Given the encapsulation, and the need for antennae, the smallest of these devices is believed to be just less than 0.84 mm by about 3 or 4 mm. As the transponder trigger is radio waves, typically there is no substantial issue with the orientation of the transponder once injected.

To take advantage of small size, simplicity and stability of the light-triggered devices, these are preferably implanted without encapsulation. The devices are rendered biologically inert in the semiconductor foundry fabrication process, where a passivation layer of silicon oxide is applied to the otherwise finished device This leaves the devices only susceptible to physical damage or misorientation in the implantation process. Accordingly, what is needed are implantation injectors that provide a minimum of trauma to the animal consistent with the small size of the light-triggered devices, provide for a high success rate for implantation, and provide for an oriented implantation such that the photovoltaic elements of the microchips are oriented to be accessible for triggering.

SUMMARY

Embodiments of the present invention generally relate to methods for subcutaneously delivering a sided, planar microchip and devices for effecting such delivery.

Provided, among other things, is an injector system adapted for injecting a microchip comprising: an inserter comprising a rod or tube having a proximal and distal end and having a point at the distal end that defines a skin-piercing side of the inserter; a means for engaging the microchip near the distal end of the inserter, but removed in the proximal direction from the distal tip of the inserter, which means prevents rotation of an engaged microchip in two or three axes of rotation; and means for releasing the microchip from the inserter once the inserter has been pierced into a perforatable substrate.

Further provided is method of injecting a microchip comprising: providing the injector system adapted for use with the microchip; inserting the distal end of the inserter into a perforatable substrate; and activating the means for releasing to leave the microchip in the substrate.

Additionally provided is an injector kit comprising: an injector system comprising (a) an inserter comprising a rod or tube having a proximal and distal end and having a point at the distal end that defines a skin-piercing side of the inserter; and (b) a means for engaging the microchip near the distal end of the inserter; and a mildly adhesive film or polymer solution adapted to stabilize the engagement of the microchip with the means for engaging.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIG. 1A schematically depicts a top view of an inserter of the invention, while

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

A sided microchip is one for which its orientation upon implantation has a functional consequence. A microchip has a length, width and height. A planar microchip is one where the height is 50% or less than the smallest of the length or width. In some embodiments, the height is 40% or less, 35% or less, 30% or less, 25% or less, or 20% or less, than the smallest of the length or width. Microchips used in the invention are often, but not necessarily, square or rectangular, consistent with a focus on low cost of production. A microchip is one where the longest of the length or width is 1.2 mm or less. In some embodiment, the longest of the length or width is 1.1 mm or less, 1.0 mm or less, 0.9 mm or less, 0.8 mm or less, 0.7 mm or less, or 0.6 mm or less, or 0.5 mm or less, or 0.4 mm or less, or 0.3 mm or less, or 0.25 mm or less, or 0.2 mm or less. In one embodiment, the microchip is 600 micron×600 micron×100 or 120 micron, or 500 micron×500 micron×100 or 120 micron.

In certain embodiments, the inserter comprises a needle, i.e., a rod-like or tubular structure with a pointed or beveled end adapted to pierce skin or another substrate that is similarly susceptible to piercing. In certain embodiments, the inserter has a notch or alcove adapted to fit the sided, planar microchip.

Figure 1A:
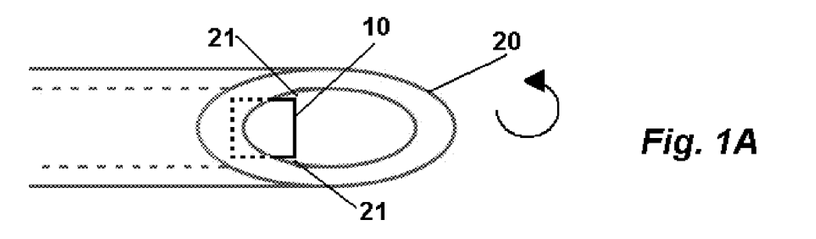
Figure 1B:
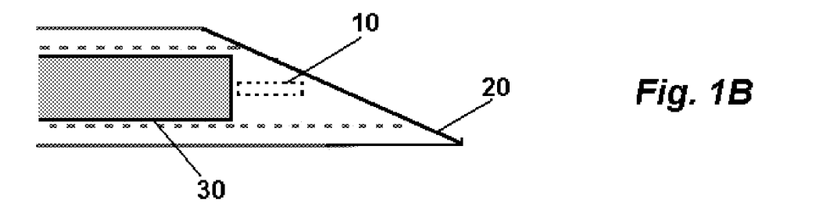
FIG. 1B shows a side view.

In one embodiment, as illustrated in FIGS. 1A and 1B, the injector system comprises a beveled inserter 20 (in this case, a hollow needle), sized so that when microchip 10 is inserted in a cavity therein it cannot substantially rotate in the plane illustrated with the arrow. This is the plane substantially parallel with the major faces of the microchip, which can be deemed the "plane of the microchip." Without such rotation, the microchip does not have enough freedom of movement to readily invert (e.g., so that the top face, say facing outward, can flip so that it faces inward). Typically, though not necessarily, the face that would be upwards, from the perspective of FIG. 1A, is that with the photo-sensitive elements. To facilitate stable placement, a mildly adhesive polymer solution can be place on the edges of the microchip, say at positions 21. After the needle is inserted in the intended substrate, such as skin, pusher 30 can be used to push the microchip out of the injector. The pusher can be movement limited so that it extends outward about as far as needed so that the microchip is retained by the substrate when the injector system is withdrawn from the substrate.

The mildly adhesive polymer solution should, in biological applications, be biocompatible. For example, carboxymethyl cellulose, methyl cellulose, cellulose polymers, high molecular weight (200,000 or >) polyethylene glycol, high molecular weight (200,000 or >) dextran, or the like can be used. For carboxymethyl cellulose, for example, a 2% w/v solution can be used or for example, or a 10% w/v solution can be used. The mildly adhesive polymer solution can be used with any of injector the embodiments described herein to further stabilize the microchip. The mildly adhesive polymer solution can be to withstand heat sterilization, such as sterilization by autoclave, while retaining a functional amount of adhesiveness. A "mildly" adhesive material will be recognized as one adhesive enough to provide the stabilization described herein, but not so adhesive as to interfere with release of the microchip.

In certain embodiments, a readily displaced film is affixed over the opening to the cavity in which the microchip is seated. Such a film can be of a soft or flexible polymer, a waxy substance, or the like. The film can be affixed with an adhesive that can be displaced by the injection process, or by the adhesiveness of the film (e.g., a waxy film). The film can substitute for the mildly adhesive polymer, and can itself be mildly adhesive. Where the film can be injected with the microchip, and where a biological substrate for injection is intended, a biocompatible material can be selected for the film.

The Figures, particularly such figures as FIGS. 1A-3C, 4 and 6A, are conceptual. For example, the skin-piercing end may be more pointed than indicated.

Figure 10:
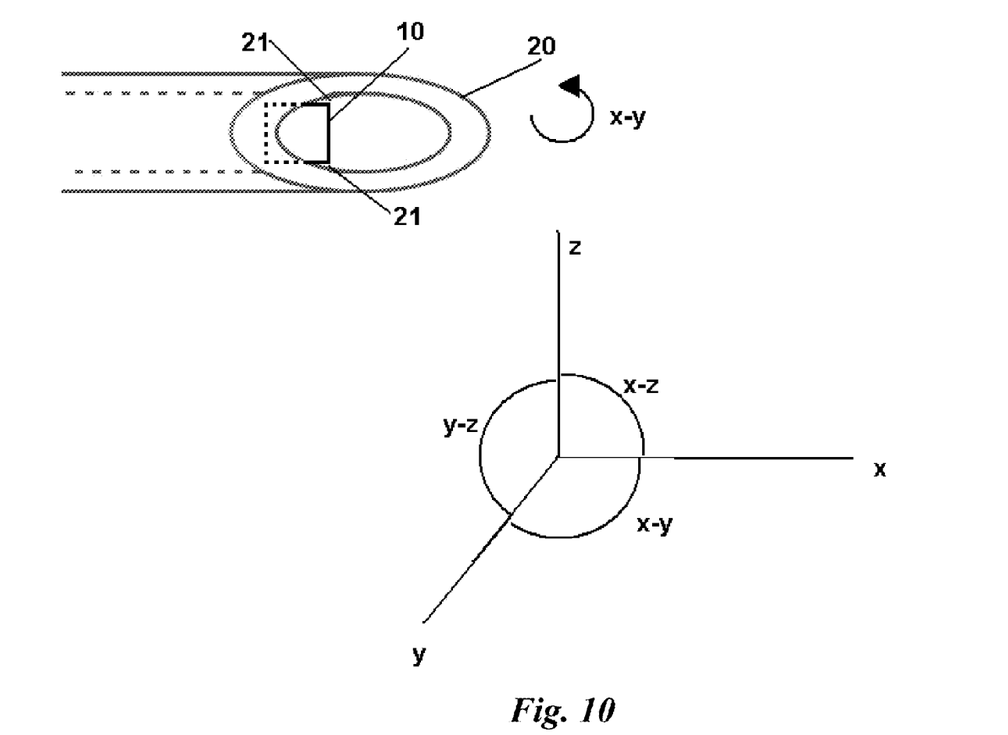
FIG. 10 shows the embodiment of FIG. 2A aligned with a coordinate system.

Axes of motion can be described by reference to the embodiment of FIG. 1A aligned with an x-y-z coordinate system, as in FIG. 10. The main axis of the inserter is aligned with the x axis. In the FIG. 1A embodiment, the microchip is somewhat free to rotate in the y-z axis, but restricted in the other two axes. The use of a mildly adhesive polymer or film limits y-z rotation. In other embodiments, rotation in all three axes can be restricted.

The substrate is a perforatable substrate, meaning that it is comparable to epithelial tissue, soft material, or soft plastic, (e.g. a sheet of silicone rubber) in its susceptibility to being perforated.

Figure 2A:
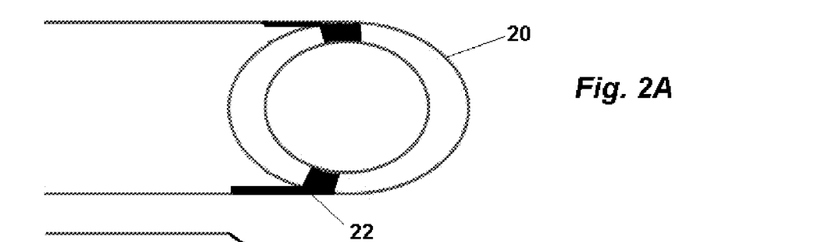
FIG. 2A illustrates a top view of an inserter of the invention.
Figure 2B:
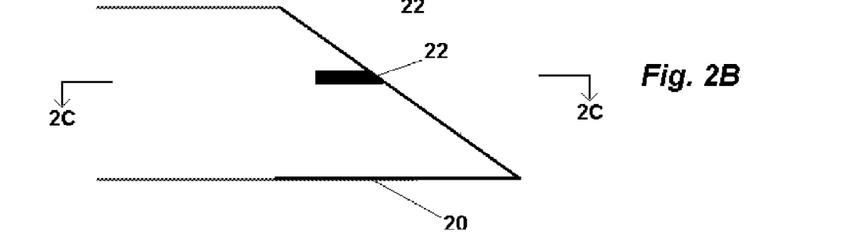
FIG. 2B shows a side view.
Figure 2C:
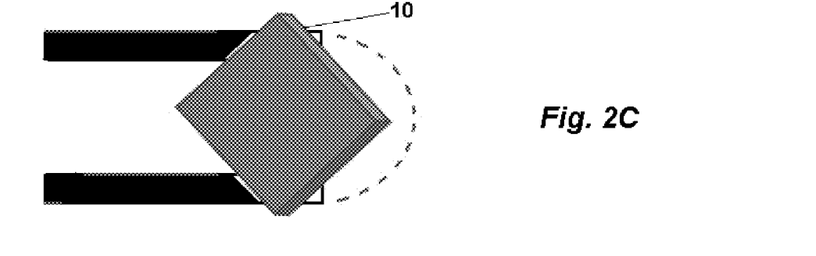
FIG. 2C shows a cut-away view.

In certain embodiments, the inserter 20 has a slot formed in it to accommodate the microchip. For example, in FIG. 2A-C, the slot 22 is formed in the inserter 20 such that its width is close to the height of the microchip 10, so that the microchip fits therein with a measure of tightness (which may be augmented by adhesive or film). As the cut-away of FIG. 2C shows how the slot, in this embodiment, is formed to fit the chip so that an edge of the microchip is oriented towards the tip of the inserter. In FIG. 2C, the dark portions of inserter 20 indicate the upper part of the cutaway, while the white indicate the lower floor of the slot 22.

A microchip generally has two recognizable major axes (say, x and y). If the microchip fits in the inserter so that the major axes are adapted to enter the substrate parallel (e.g., x) and perpendicular (e.g., y) to the major axis of the inserter, as in FIG. 1, the microchip is seated on-axis. If not, as in FIG. 2C, the microchip is fitted off-axis.

Figure 3A:
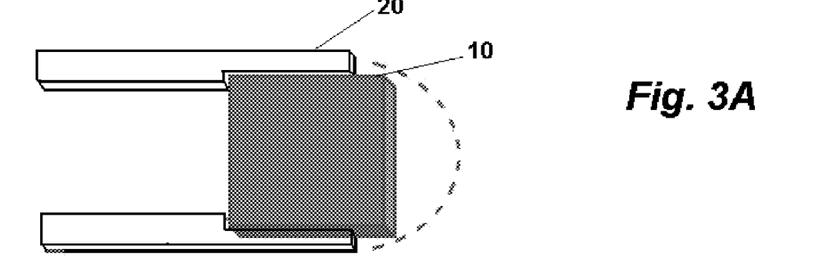
FIGS. 3A and 3B show cut-away views of inserters of the invention.
Figure 3B:
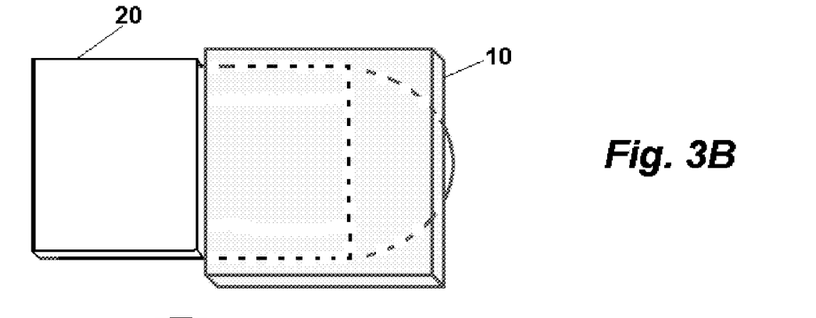
Figure 4:
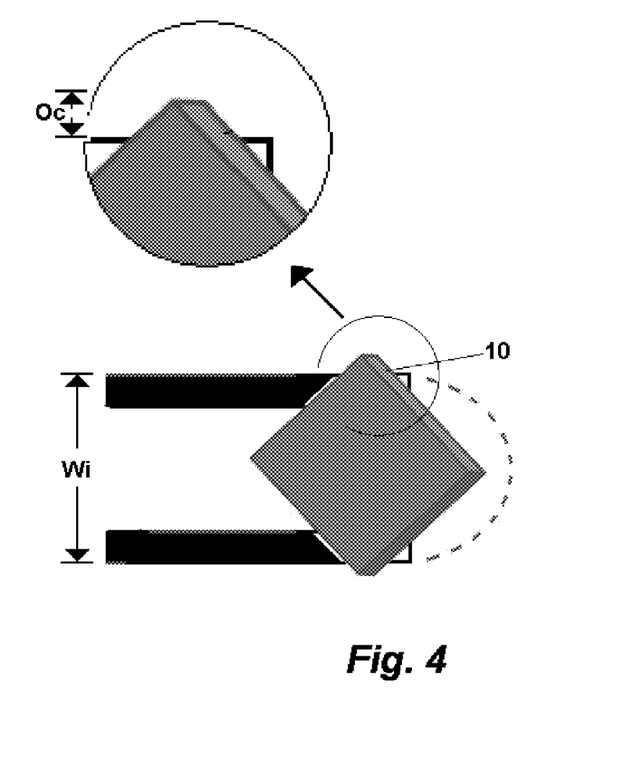
FIG. 4 shows a cut-away view of an inserter of the invention.

As can be seen, for example, in FIGS. 3A-3B (which show cutaways comparable to that of FIG. 2C), the slot can be formed in a manner adapted to hold the microchip in different geometries. The slot can be, as in FIG. 3A, totally internal to the inserter 20. The slots can be formed by electro discharge machining, electrochemical machining, water jet cutting, laser cutting, more conventional mechanical machining methods, molding methods, or the like. The choice of particular cutting or molding methods will depend on the material of the inserter. (Depth in these figures is indicated by rough perspective lines.)

One can define the concept of "coverage" with reference to the drawings. In the inserters having a hollow core, one can conceive of the corresponding structure with a solid core (except where the microchip sits). Coverage is the percent of area on the two major surfaces of the microchip that would sit inside the so-conceived injector. Where the injectors are actually solid except for any slot, coverage is the percent of area on the two major surfaces of the microchip that sits inside the injector. Where there is a sloped surface as the inserter transitions from the substrate-piercing distal end back to a generally thicker portion of the inserter, that slope is extended through where the microchip seats, with that imaginary extension defining the boundary of what is inside and outside the inserter. In certain embodiments, coverage is 25% or more, 30% or more, 35% or more, 40% or more, 45% or more, 50% or more, 55% or more, or 60% or more. Where coverage is 50% or more, the microchip is substantially within the inserter. In some embodiments, coverage is 100%.

Figure 6A:
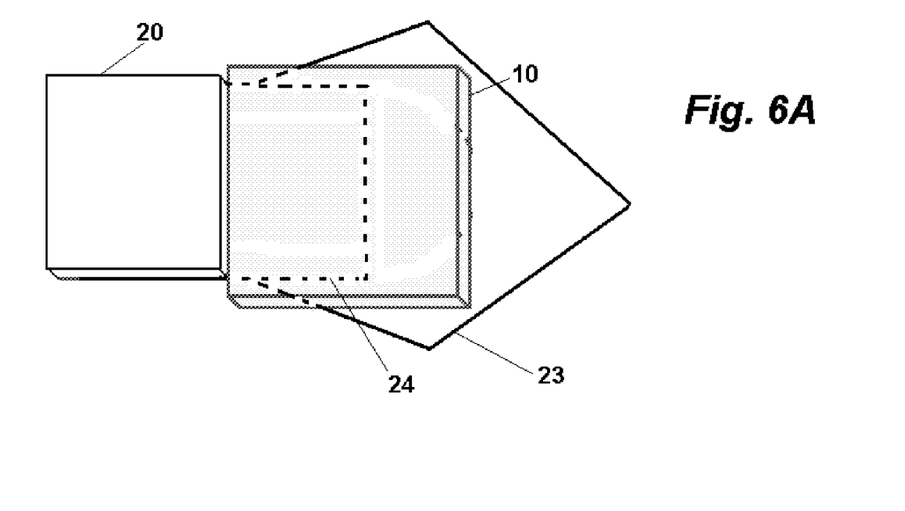
FIGS. 6A and 6B show cut-away and perspective views, respectively, of an inserter of the invention.

In certain embodiments, the microchip seats so as to overhang the width of the inserter. The overhang distance, Oc (FIG. 4) is, in certain embodiments, 35% or less of the inserter width Wi. Inserter width is the predominant width of the inserter, without regard to brief expansions at the distal end of the inserter, so long as the expansions are not situated to eliminate the overhang. This concept is illustrated in FIG. 6A, where the expansion covers the overhang at the distal end of the microchip, but not at the near end. In certain embodiments, the overhang distance is 30% or less, 25% or less, 20% or less, or 15% or less of the inserter width. In certain embodiments, the overhang distance is 5% or more, 10% or more, 15% or more, or 20% or more of the inserter width. In certain embodiments, the overhang comprises a barb function that mechanically resists being withdrawn from the injection substrate.

Figure 5A:
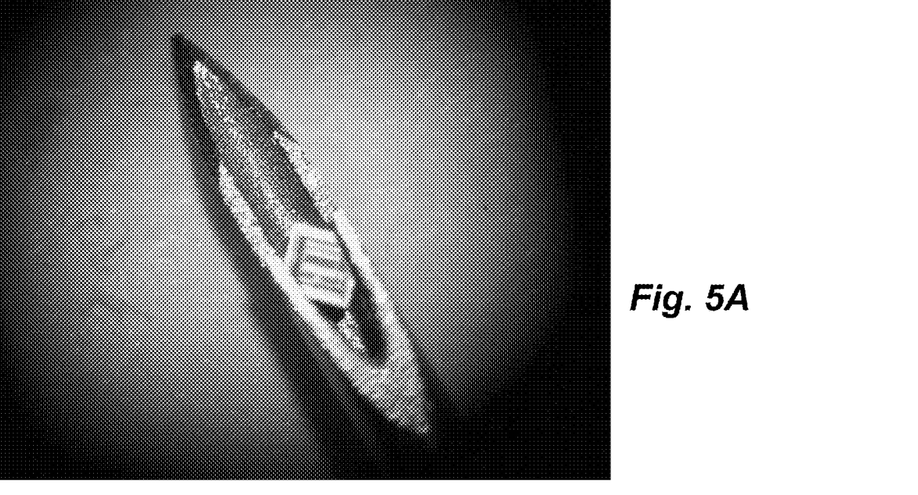
FIG. 5A depicts an inserter of the invention.
Figure 5B:
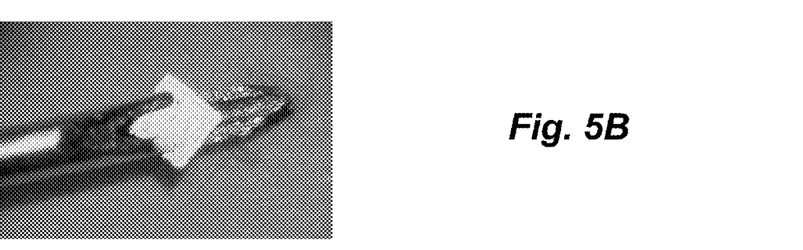
FIGS. 5B and 5C show top and side views, respectively, of an inserter of the invention.
Figure 5C:
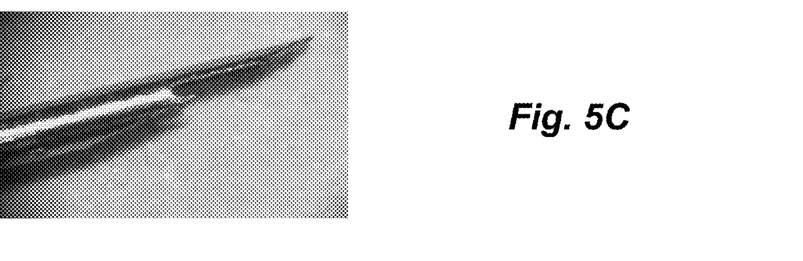

Illustrated in FIG. 5A is a slotted 21 gauge (roughly 0.819 mm O.D.) regular wall thickness needle (inserter) with an engaged microchip (face up). Illustrated in FIGS. 5B and 5C are a top and side view of a slotted 25 gauge (roughly 0.514 mm O.D.) regular thickness needle with (5B) and without (5C) a fitted microchip. In FIG. 5B the microchip is off-axis.

Figure 6B:
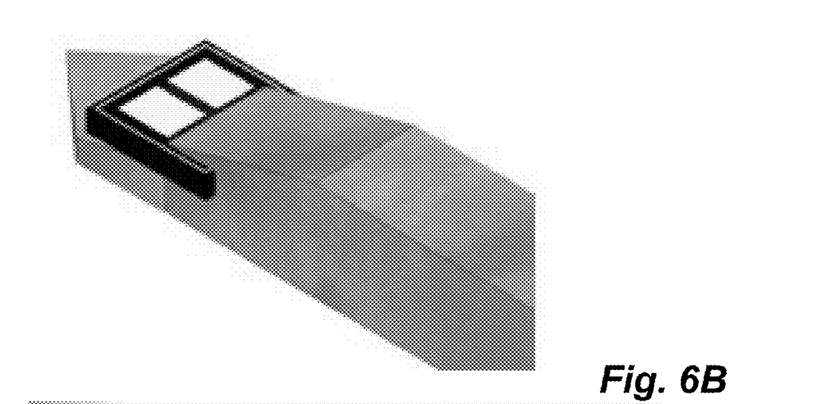

FIGS. 6A and 6B show a top, cutaway view and a perspective view of an embodiment with a distal expansion 23. The expansion can be adapted to provide for perforating the substrate to more than the width of the microchip. As in many embodiments with an overhang, the microchip overhang here is adapted to engage the injection substrate when a user withdraws the injector from the substrate, to facilitate the microchip in disengaging the inserter and seating in its injected location. This embodiment can be made with the same machining methods described above. In some embodiments, the injector is solid; in others, the inserter is hollow to allow for a pusher. This embodiment has an overhang, since the barb does not define the predominant width of the inserter.

For slotted embodiments, for example made from hypodermic needles, the pusher can be made by cutting a narrower gauge needle rod that fits inside the needle that holds the chip to an appropriate insertion length. This needle-based version assumes a round channel. Other machining methods can be envisioned with other geometries (e.g., square, rectangular, multifaceted).

Figure 7:
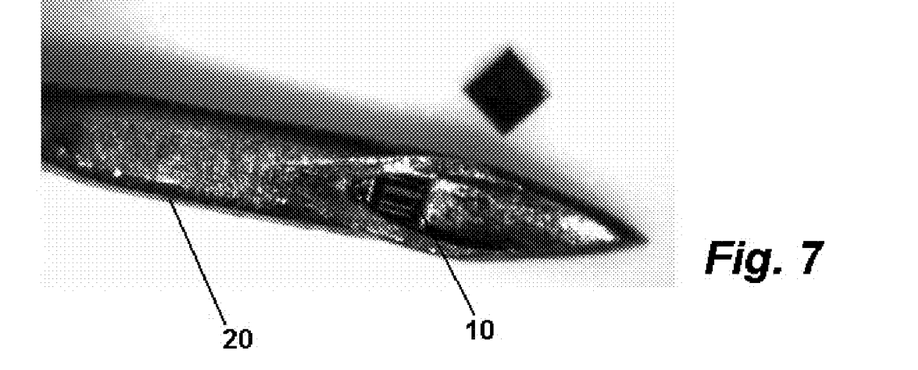
FIG. 7 depicts an inserter of the invention.

In certain embodiments, the injector is analogous to flattened hypodermic needle. Illustrated in FIG. 7 is a 21 gauge thin walled needle that has been flattened at the distal end, together with an inserted (illustrated with 100% coverage) microchip (approximately 600 nm×600 nm×100-120 nm). The depth of insertion can be controlled with the pusher, inserted to its starting depth of insertion into the inserter. Given the size of the illustrative microchip, a 20 or 21 gauge needle (e.g., BD IV 1.5" 21 gauge thin walled needle, BD part number 305190) is appropriate to allow microchip insertion without the microchip having rotational freedom. Other sizes and wall thicknesses may be appropriate. These needles can be referred to as "flat-tip" needles.

A flat-tip needle allows a chip to fit inside a smaller diameter needle than an unmodified needle while retaining the chip in the desired orientation within the injector. In addition, a flat-tip needle is more suitable for piercing a very thin substrate such as the thin layer of skin or the like.

Thin walled, or ultra thin walled needles can be useful for allowing microchips to be fitted in smaller sized needles.

Figure 8:
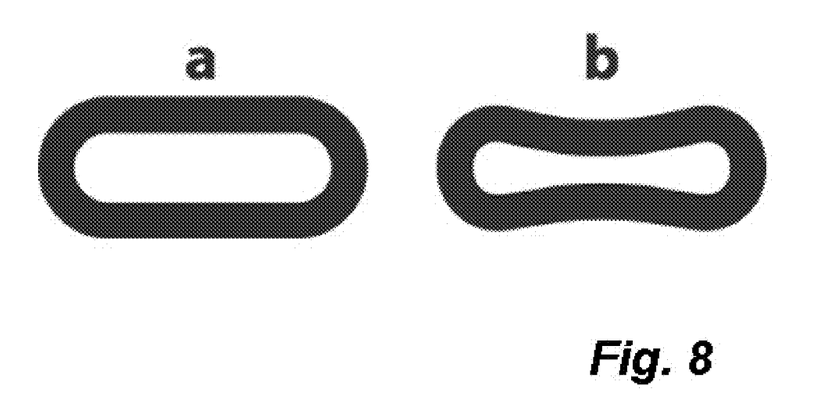
FIGS. 8A and 8B show a desirable and less desirable cross-section for an inserter of the invention.

When the flattened needle is made by compressing a hypodermic needle, care can be taken so that the cross-section of the flattened needle is predominantly similar to FIG. 8A rather than FIG. 8B. For example, thin walled stainless steel tubing, when crushed perpendicular to the radius, results in the FIG. 8 shaped cross-section in FIG. 8B. To avoid this effect, high temperature tempering can be used to soften the steel. When flattened the resultant shape was much closer the optimal shape as shown in FIG. 8A. (Note that while the FIG. 8B cross-section is less elegant, one can picture how it can function with an appropriately sized microchip and an appropriately sized pusher. Even if there were some play in the movement of the microchip at the edges, the microchip would still be rotationally constrained and would effectively engage the pusher.)

An exemplary methodology for forming a flattened injector system was as follows:

Step 01: The needle tip was heated with a blowtorch until it glowed orange. The tip was then left to cool in air. After the heating, the tip is slightly blackened. This black residue is easily buffed off later.

Step 02: The needle was then partially flattened by gently squeezing the needle in a vise.

Step 03: A 0.008" shim (cut from 0.008" metal sheets) was then inserted as far as it would go into the needle.

Step 04: The needle was then reinserted into the vise and flattened a second time until resistance was felt.

Step 05: The shim was removed (if the shim is not easily removed, the pressure used in the flattening was probably too high).

Step 06: The pusher was prepared from a higher gauge needle or needle rod in a similar way, heat treating and flattening in a vise.

Step 07: The needle and pusher were buffed using a felt pad attachment and a Dremmel tool, available at Home Depot and Sears.

Step 08: The needle and pusher were put in an ultrasonic bath for 20 minutes in denatured ethanol. Steps 7 and 8 resulted in clean needles.

Step 09: The pusher handle was made from the plastic Luer-Lok end of an unused 21 gauge needle. The original needle was notched with a file and broken off close to the plastic.

Step 10: The plastic Luer-Lok end was trimmed so that it would fit into the Luer-Lok plastic end of the inserter needle (from step 8). In particular, the Luer-Lok end was mounted on a syringe for handling and trimmed to remove plastic wings that would prevent fit with the Luer-Lok plastic end of the inserter needle.

Step 11: The pusher was inserted into the pusher handle, and the flattened end of the pusher was adjusted so that, as fully inserted, it would push a microchip out of the inserter without overextending into the injection substrate.

Step 12: The pusher was then glued to the plunger handle using HySol adhesive, Loctite number 1C-LV which is available from McMaster, (part number 6430A35). This epoxy adhesive was left to harden.

Step 13: Any protruding tip of the pusher was snipped off with a wire cutter.

Step 14: To protect the user from possible sharp edges the distal end of the pusher was coated with a drop of Plasti-Dip (UPC 0-75815-11603-1, available from Home Depot).

The shim material, e.g. of thickness 0.008" but cut to a narrower width, can also be used as the distal end of the pusher. Such shim material can be joined to proximal segment of the pusher by, for example, laser welding.

When using metal tubing, the inserter can be formed, for example, from rectangular or oval profiled tubing, such as available from Attica Components Limited (North Leigh, UK), New England Small Tube Corporation (Litchfield, N.H.) or Metal Cutting (Cedar Grove, N.J.). Such rectangular or oval profiled tubing can be made by extrusion. An appropriate bevel can be formed by the machining methods discussed above. As needed, the tubing can be connected to another piece of tubing by, for example, laser welding.

While inserters formed of metallic tubing are useful, inserters can be formed of other materials, such as suitably rigid plastics, glasses, composites, or the like. Plastic inserters can be formed by extrusion, molding, and machining.

Care should be taken that the pusher is sized so that it cannot fit above or below the microchip when the microchip is appropriately seated in the injector.

All of the forms of retaining the microchip described herein prevent an appropriately engaged rectangular or oblong microchip from rotating in the plane of the microchip. For a round microchip, the embodiment of FIG. 1 can use of adhesive to provide such rotational restraint.

The microchips can be naked (but for the passivation layer), or they can be directly coated with a suitable polymer. Such polymers include, for example, parylene, silane, or polyethylene glycol. Parylene can, for example, be applied by chemical vapor deposition of di-p-xylylene. The coating can be selected to improve one or more of biocompatibility, the insertability (e.g., due to lubrication) of the microchip, or stability. In some embodiments, the polymer layer could substitute for the passivation layer.

Figure 9A:
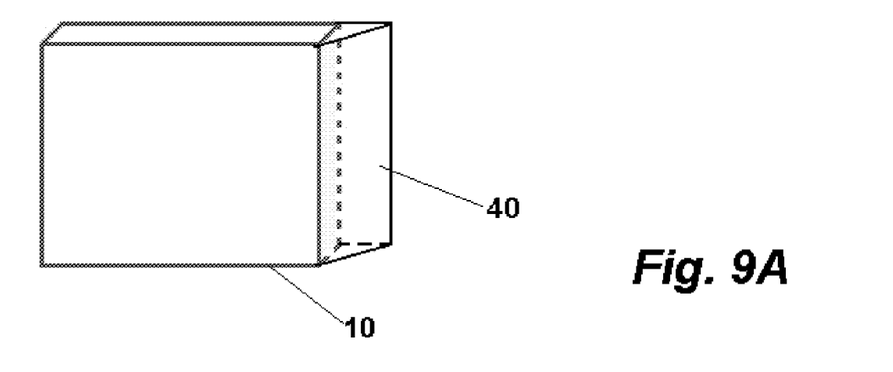
FIGS. 9A and 9B show exemplary wedges on microchips.
Figure 9B:
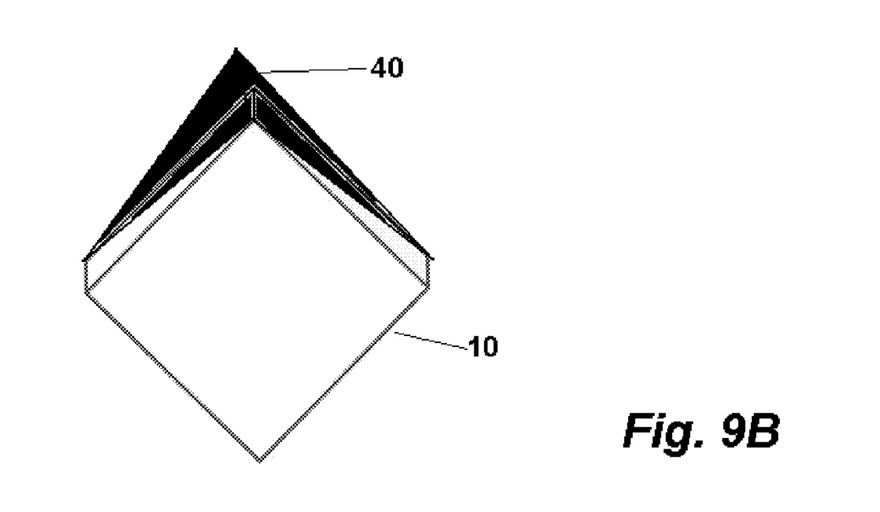

The microchips can also be formed to have or be fitted with a wedge 40, as illustrated in FIGS. 9A and 9B. The wedge can be oriented towards the injection substrate, typically with the wedge geometry selected for compatibility with the bevel or the like of the inserter. The wedge can be formed, for example, of a suitable plastic adhered to the microchip. Or, the microchip can be placed in a carrier form (having a slot for the microchip) that provides wedge geometry.

Encapsulation, for the purposes of this application, is insertion into a preformed container (e.g., of two parts that fit together). The injector system of the current invention typically injects a microchip that is not encapsulated. Note that the direct coating or wedge addition does not comprise encapsulation.

The injector system can be tested for example by injection into a ~1 mm thick piece of silicone rubber. The puncture angle should be <5°, such as about 2° by estimation, to assure that the microchip is not injected too far into the substrate. Typically, the inserter goes in microchip up and bevel pointing towards the substrate. Once the microchip is underneath the silicon, the pusher is gently engaged to push the microchip out of the inserter (if the inserter design uses a pusher). The inserter is then withdrawn and the microchip read.

The invention also comprises methodology. For example, the inserter is provided with or loaded with a microchip, then used to pierce a substrate and delivery the microchip under the surface of the substrate. If present, the pusher is activated to separate, or begin to separate, the microchip from the inserter. The inserter is removed from the substrate, leaving the microchip. It may be that the pusher only partially separates the microchip, but enough so that the microchip sufficiently engages with the substrate so that it does not withdraw with the inserter. In some embodiments with a pusher the inserter is withdrawn after the pusher is activated; in others the pusher is activated in conjunction with drawing the inserter. Injection can be facilitated by applying a suitable lubricant (e.g., mineral oil) to the loaded inserter tip.

The substrate can for example be animal epithelial tissue, including human epithelial tissue (for example, for use with patients with dementia and therefor in potential need of an identifying device). For the purposes of this application, "epithelial tissue" is such epithelial boundary tissue and any underlying tissue where a light-triggered transponder can be delivered and subsequently triggered by a reader located on the outside of the epithelial layer. Other potential uses with humans can be to provide a security identifier.

The injection methods are useful with small laboratory animals, such as rabbits, hamsters, rats and mice.

When injecting into a mouse or rat tail, the microchip can be injected on top of the section of cartilage that is in the side of the tail. The pigmentation is generally lighter in this location, so that it is easier to see and read the microchip after injection. This injection site also prevents nicking the tail vein. The mouse is restrained. The tail can be wiped with 70% ethanol or other suitable disinfectant. While holding the tail taut, the line of cartilage along the right side of the tail is then localized by a slight rotation of the tail. The needle is inserted 1-2 cm from the base of the tail at an angle almost parallel to the tail, until the bevel is under the skin. The injector is typically oriented with the bevel upright and pointed toward the animal. The plunger is then pushed to gently insert the microchip and the needle removed and disposed. The microchip is then read, and the animal "registered" in tracking software. This entire process can take less than one minute and does not require anesthetics or tranquilizers.

Two-part molds can be constructed to effect the needle narrowing method described above with 14 exemplary steps. For example, a first mold can be designed to provide the initial narrowing and no more—because the two mold pieces, fully engaged together, provide no more than the initial narrowing. The shim can be engaged in the compressed needle channel, and the needle given a final compression in a second mold adapted to provide exactly the sought-for amount of narrowing. The pusher can be made in a third mold, generally in one compression step, since a shim is not required.

The means for engaging include for example a traditional needle with adhesive polymer, slots 22 (e.g., seating the microchip internally or partly externally), needles shaped to prevent y-z rotation, and the foregoing with adhesive polymer. The means for releasing include for example a pusher 30 and an overhang of the microchip relative to the inserter such that the overhang provides a barb function.

While the foregoing is directed to embodiments of the present invention, other and further embodiments of the invention may be devised without departing from the basic scope thereof, and the scope thereof is determined by the claims that follow. Any claim below that is written as dependent on an independent claim can also be written as dependent on any of the claims under such independent claim, except where logic forecloses such a dependency.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. An injector system adapted for injecting a planar microchip having a top major face, the system comprising: the planar microchip; and
    an inserter comprising a rod or tube having a proximal and distal end and having a point at the distal end that defines a skin-piercing side of the inserter;
    a means for engaging the microchip near the distal end of the inserter, but removed in the proximal direction from the distal tip of the inserter, which means prevents rotation of an engaged microchip in two or three axes of rotation; and
    means for releasing the microchip from the inserter once the inserter has been inserted into a perforatable substrate,
    wherein the rotation prevention allows the injector system to inject the microchip into a perforatable substrate with a pre-determined orientation for the top major face.

2. The injector system of claim 1, wherein the means for engaging the microchip prevents rotation of an engaged microchip in three axes of rotation.

3. The injector system of claim 2, wherein the means for releasing comprises the microchip being adapted to engage the inserter with an edge of the microchip on both sides of the inserter situated to act as a retaining barb that mechanically resists being withdraw from the substrate.

4. The injector system of claim 3, wherein the means for releasing further comprises a pusher that pushes on the microchip to at least partially release the microchip from the inserter.

5. The injector system of claim 3, wherein the distal end of the inserter comprises an expansion adapted to provide for perforating the substrate to more than the width of the microchip.

6. The injector system of claim 2, wherein the means for releasing comprises a pusher that pushes on the microchip to at least partially release the microchip from the inserter.

7. The injector system of claim 6, wherein the means for engaging the microchip comprises a cavity in the inserter having lateral walls shaped to block rotation of an engaged microchip, wherein the inserter and the engaged microchip are adapted so that the microchip is substantially within the inserter.

8. The injector system of claim 7, wherein the lateral walls of the cavity are shaped to block the rotation of an engaged microchip in any direction.

9. The injector system of claim 7, wherein the inserter and the engaged microchip are adapted so that the microchip is fully within the inserter.

10. The injector system of claim 1, wherein the means for engaging the microchip comprises a slot in the inserter into which an edge of the planar microchip is inserted.

11. The injector system of claim 10, wherein the means for releasing comprises the microchip being adapted to engage the inserter with an edge of the microchip on both sides of the inserter situated to act as a retaining barb that mechanically resists being withdraw from the substrate.

12. The injector system of claim 11, wherein the means for engaging the microchip is adapted to engage the microchip off-axis.

13. The injector system of claim 11, wherein the means for releasing further comprises a pusher that pushes on the microchip to at least partially release the microchip from the inserter.

14. The injector system of claim 13, wherein the means for engaging the microchip is adapted to engage the microchip off-axis.

15. A method of injecting a microchip comprising:
providing the injector system of claim 1 adapted for use with the microchip;
inserting the distal end of the inserter into a perforatable substrate; and
activating the means for releasing to leave the microchip in the substrate with the pre-determined orientation of the top major face.

16. The method of claim 15, wherein the perforatable substrate is an animal.

17. The method of claim 15, wherein the perforatable substrate is a small laboratory animal.

18. The method of claim 17, wherein the perforatable substrate is tail or ear epithelial tissue of the small laboratory animal.

19. An injector kit comprising: a single planar microchip having a top major face; and
an injector system for injecting the single planar microchip, the system comprising
an inserter comprising a rod or tube having a proximal and distal end and having a point at the distal end that defines a skin-piercing side of the inserter; and
a means for engaging the single microchip near the distal end of the inserter, adapted to restrict x-y and x-z rotation of the planar microchip; and
a mildly adhesive polymer solution adapted to stabilize the engagement of the microchip with the means for engaging,
wherein the polymer solution limits any y-z rotation of the planar microchip,
wherein the injector system injects the microchip into a perforatable substrate with a pre-determined orientation for the top major face.

* * * * *